US010457716B2

(12) United States Patent
Baker et al.

(10) Patent No.: US 10,457,716 B2
(45) Date of Patent: Oct. 29, 2019

(54) PROTEIN FOLDING AND METHODS OF USING SAME

(71) Applicant: THE UNIVERSITY OF NOTRE DAME du LAC, Notre Dame, IN (US)

(72) Inventors: Brian M Baker, Granger, IN (US); Lance Hellman, Granger, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 492 days.

(21) Appl. No.: 14/820,290

(22) Filed: Aug. 6, 2015

(65) Prior Publication Data

US 2016/0039907 A1 Feb. 11, 2016

Related U.S. Application Data

(60) Provisional application No. 62/033,861, filed on Aug. 6, 2014.

(51) Int. Cl.

| | | |
|---|---|---|
| *C07K 14/74* | (2006.01) |
| *B01D 15/38* | (2006.01) |
| *C07K 1/113* | (2006.01) |
| *C07K 1/34* | (2006.01) |
| *B01D 15/34* | (2006.01) |
| *B01D 15/36* | (2006.01) |
| *B01D 15/32* | (2006.01) |

(52) U.S. Cl.
CPC .... *C07K 14/70539* (2013.01); *B01D 15/3804* (2013.01); *C07K 1/1136* (2013.01); *C07K 1/34* (2013.01); *B01D 15/327* (2013.01); *B01D 15/34* (2013.01); *B01D 15/361* (2013.01); *C07K 2319/21* (2013.01)

(58) Field of Classification Search
CPC .. A61K 39/00; A61K 38/00; A61K 2039/605; G01N 33/56977; G01N 2333/70539
See application file for complete search history.

(56) References Cited

U.S. PATENT DOCUMENTS

| | | | |
|---|---|---|---|
| 4,530,787 A | 7/1985 | Shaked et al. | |
| 4,620,948 A | 11/1986 | Builder et al. | |
| 6,007,820 A | 12/1999 | Nag | |
| 8,703,123 B2 | 4/2014 | Hinderer et al. | |
| 2002/0058614 A1* | 5/2002 | Filvaroff | A61K 9/5031 514/6.5 |
| 2004/0011663 A1 | 1/2004 | Bossoutrot | |
| 2004/0166546 A1* | 8/2004 | Warmington | C07K 14/40 435/7.31 |
| 2008/0014208 A1* | 1/2008 | Reiter | C07K 16/30 424/179.1 |
| 2012/0237978 A1* | 9/2012 | Kobilka | C07K 14/70571 435/69.7 |

FOREIGN PATENT DOCUMENTS

| | | | |
|---|---|---|---|
| DE | WO2011113601 A1 * | 9/2011 | ........... C07K 14/535 |
| EP | 0219874 A2 | 4/1987 | |
| EP | 0364926 A2 | 4/1990 | |
| EP | 0512097 A1 | 11/1992 | |
| WO | 8605809 A1 | 10/1986 | |
| WO | 0187925 A2 | 11/2001 | |

OTHER PUBLICATIONS

Bornhorst et al. Purification of Proteins Using Polyhistidine Affinity Tags. Methods Enzymol. 2000 ; 326: 245-254. (Year: 2000).*
Witkowska et al. Antibodies against human muscle enolase recognize a 45-kDa bacterial cell wall outer membrane enolase-like protein. FEMS Immunology and Medical Microbiology 45 (2005) 53-62. (Year: 2005).*
Singh et al. Solubilization and Refolding of Bacterial Inclusion Body Proteins. J Biosci Bioeng. Apr. 2005;99(4):303-10. Review. (Year: 2005).*
Loi Cheng. In Vitro Expression and Purification of Class I MHC Molecules. Thesis. Spring May 3, 2006 (Year: 2006).*
Trinkle-Mulcahy et al. Identifying specific protein interaction partners using quantitative mass spectrometry and bead proteomes. J Cell Biol. Oct. 20, 2008;183(2):223-39. (Year: 2008).*
Camacho-Carvajal et al. Two-dimensional Blue native/SDS gel electrophoresis of multi-protein complexes from whole cellular lysates: a proteomics approach. Mol Cell Proteomics. Feb. 2004;3(2):176-82. Epub Dec. 9, 2003. (Year: 2004).*
Thermo Scientific Pierce High-Performance Dialysis, Desalting and Detergent Removal Technical Handbook. Dec. 2009. Thermo Fisher Scientific Inc. (Year: 2009).*
Parham et al. Use of a monoclonal antibody (W6/32) in structural studies of HLA-A,B,C, antigens. J Immunol. Jul. 1979;123(1):342-9. (Year: 1979).*
Garboczi et al. HLA-A2-peptide complexes: refolding and crystallization of molecules expressed in *Escherichia coli* and complexed with single antigenic peptides. Proc Natl Acad Sci U S A. Apr. 15, 1992;89(8):3429-33. (Year: 1992).*
Reid et al., Production and crystallization of MHC class I B allele single peptide complexes, FEBS Letters, 1996, pp. 119-123, vol. 383, Federation of European Biochemical Societies.

(Continued)

*Primary Examiner* — Marcela M Cordero Garcia
*Assistant Examiner* — Jia-Hai Lee
(74) *Attorney, Agent, or Firm* — Denise L. Mayfield; Husch Blackwell LLP

(57) ABSTRACT

The instant disclosure provides a microscale method for providing correctly folded, and assembled biologically active proteins in an efficient and shorted time frame, compared to conventional protein production techniques. Proteins produced from inclusion bodies and other aggregated protein sources are provided. Microscale production of correctly folded and assembled class I MHC protein and complexes thereof are also provided for, as well as for high throughput production for use in epitope discovery protocols. Microscale production of complex proteins from protein aggregates and preparations containing protein aggregates is provided that requires less than 24 hours of processing time.

17 Claims, 5 Drawing Sheets

(56) References Cited

OTHER PUBLICATIONS

Richard R. Burgess, Refolding Solubilized Inclusion Body Proteins, Methods in Enzymology, 2009, pp. 259-282, vol. 463, Elsevier Inc.

Davis-Harrison et al., Two Different T Cell Receptors use Different Thermodynamic Strategies to Recognize the Same Peptide/MHC Ligand, Journal of Molecular Biology, 2005, 21 Pages, vol. 346, Elsevier Ltd.

Morgan et al., Circular dichroism determination of class I MHC-peptide equilibrium dissociation constants, Protein Science, 1997, pp. 1771-1773, vol. 6, The Protein Society, Cambridge University Press, USA.

Seras-Franzoso et al., Bacterial Inclusion Body Purification, Chapter 16 of Insoluble Proteins: Methods and Protocols, 2015, pp. 293-305, vol. 1258, Springer Science+Business Media, New York, USA.

Anton Simeonov, Recent developments in the use of differential scanning fluorometry in protein and small molecule discovery and characterization, Expert Opinion on Drug Discovery, 2013, pp. 1071-1082, vol. 8 Issue 9, Informa UK, Ltd.

Singh et al., Solubilization and Refolding of Bacterial Inclusion Body Proteins, Journal of Bioscience and Bioengineering, 2005, pp. 303-310, vol. 99 Issue 4, The Society for Biotechnology, Japan.

Trolle et al., Automated benchmarking of peptide-MHC class I binding predictions, Bioinformatics, 2015, pp. 2174-2181, vol. 31 Issue 13, Oxford University Press.

Yamaguchi et al., Refolding Techniques for Recovering Biologically Active Recombinant Proteins from Inclusion Bodies, Biomolecules, 2014, pp. 235-251, vol. 4, MDPI, Basel, Switzerland.

\* cited by examiner

FIG. 1A
FIG. 1B
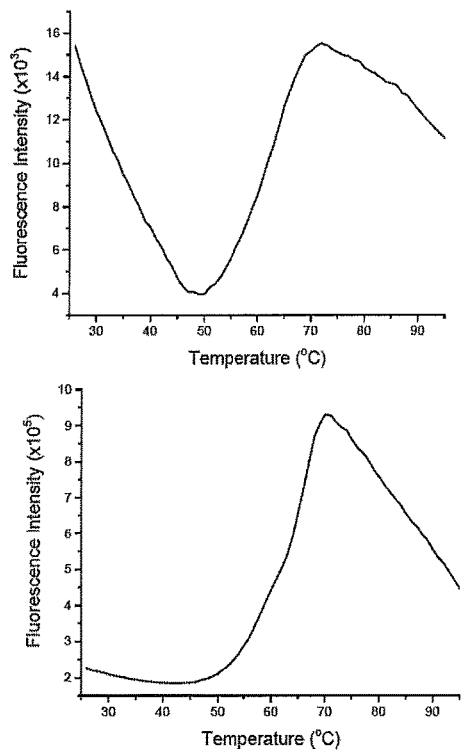
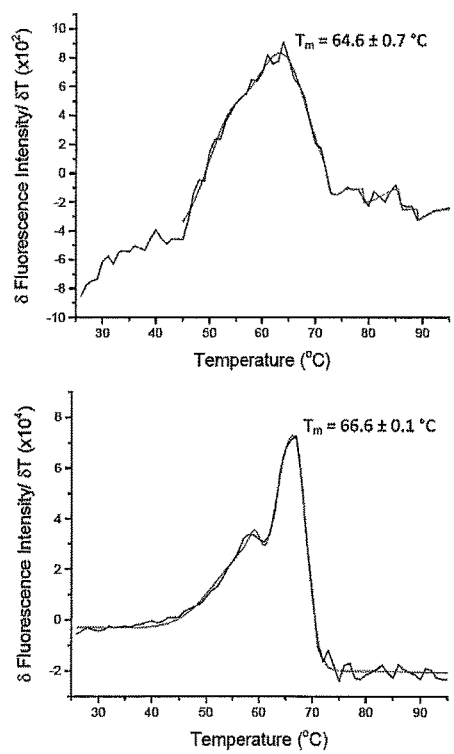
FIG. 1C
FIG. 1D

PROTEIN FOLDING AND METHODS OF USING SAME

CROSS-REFERENCE TO RELATED APPLICATIONS

Priority is claimed to U.S. Provisional Patent Application Ser. No. 62/033,861, filed Aug. 6, 2014.

This invention was made with government support under GM067079 awarded by the National Institutes of Health. The Government has certain rights in the invention.

BACKGROUND

Field

The invention relates generally to structural immunology, protein chemistry, and more particularly to in vitro protein folding.

Description of Related Art

The expression of recombinant proteins is important for the study of the biological functions of genes, the development of therapeutic drugs, and for industrial processes. There are several protein expression systems to produce the target proteins, such as bacteria, yeast, insect cells, mammalian cells, and cell-free systems. Expression in mammalian cells and insect cells produces biologically active proteins that contain post-translational modification(s), such as phosphorylation, acetylation, and glycosylation. However, expression using these systems gives low yields of the recombinant proteins, and the cost of these systems is generally expensive for industrial-scale or high throughput protein production. Cell-free systems also give low yields of recombinant proteins. Among bacterial systems, the *Escherichia coli* (*E. coli*) overexpression system is the most convenient and commonly used to produce recombinant proteins. However, expression of many proteins, particularly eukaryotic proteins, in *E. coli* leads to protein misfolding and aggregation to form inclusion bodies (Singh and Panda 2005, Burgess 2009, Seras-Franzoso, Peternel et al. 2015).

Recovering biologically active proteins at low cost is an important goal in protein folding from bacterial inclusion bodies, not only for analysis of the protein structure and function, but also for the development of therapeutic drugs and industrial processes for producing commercially relevant amounts of product. As inclusion bodies contain relatively pure and intact recombinant proteins, several approaches have been reported to recover these aggregated forms as biologically active proteins. In a typical procedure, aggregated forms are denatured and dissolved with a high concentration of denaturant, such as urea, guanidinium chloride (GdnHCl), or ionic detergents, such as N-lauroyl-sarcosine. These chemical reagents are used to decrease the non-covalent interactions between protein molecules. In addition, dithiothreitol or 2-mercaptoethanol is added to reduce undesirable inter- and/or intra-molecular disulfide bonds. Folding from denatured proteins (unfolded form) to the folded protein configurations necessary to provide biologically active proteins (folded form) occurs by the removal of denaturant. Folding efficiency (i.e., yield of folded protein) can be estimated by physical or biological activity, such as enzymatic activity, ligand binding, or spectroscopic methods if the folded state has a unique spectroscopic signal does not possess the folded protein configuration necessary to provide a biologically active protein The procedure for the removal of the denaturant from denatured proteins is a key step in the efficient folding of proteins from denatured states. Several approaches have been reported, such as size-exclusion chromatography, reversed micelle systems, zeolite absorbing systems, and the natural GroEL-GroES chaperone system. These folding methods, using chromatographic or non-chromatographic strategies, have been described in recent reviews (Singh and Panda 2005, Burgess 2009, Yamaguchi and Miyazaki 2014, Seras-Franzoso, Peternel). Although these methods work well for many inclusion body proteins and denatured model proteins, in most cases there is a significant amount of protein precipitation, resulting in a low recovery yield. Therefore, the protein folding procedure is still performed with a series of trial-and-error folding experiments.

In dialysis, a chemically denatured protein is folded by sufficiently decreasing the denaturant concentration, permitting folding. One-step dialysis (high denaturant concentration with respect to the folding buffer) is a simple method. The protein concentration remains nearly constant during the procedure. As the concentration of denaturant decreases with increased dialysis time (until equilibrium is reached), the amount of folded protein likewise increases. However, misfolding and protein aggregation will also occur, possibly due to contact between exposed hydrophobic surfaces. This suggests that a rapid decrease in denaturant concentration can initiate the formation of aggregates.

To solve this problem, step-wise dialysis has been used. In step-wise dialysis, the denatured proteins are first dialyzed to equilibrium against a high denaturant concentration, then dialyzed against a lower denaturant concentration until equilibrium is reached, and, then dialyzed against an even lower denaturant concentration. This step-wise dialysis against lower denaturant concentrations may be repeated multiple times. Such gradual removal of denaturant from the denatured proteins can achieve high folding efficiency (Yamaguchi and Miyazaki 2014). However, it is a time-consuming procedure, typically requiring multiple days. In addition, at medium denaturant concentrations the proteins can misfold or aggregate. Protein aggregation therefore remains a significant technical problem associated with the production of proteins.

The dilution method is a simple procedure used for protein folding. The denatured proteins are directly diluted multiple times with a folding buffer that does contains progressively lower or no denaturants. In the dilution method, the protein concentration is also decreased. As aggregation is a function of the protein concentration, a low protein concentration should help avoid intermolecular aggregation during the procedure. However, because proteins diffuse slower than denaturant, diluted proteins are likely to very quickly aggregate, similar to what is observed in one-step dialysis. In addition, this method requires a large volume of buffer, increasing cost and decreasing utility. Moreover, difficulties can be encountered in uniformly mixing large volumes, wherein reformation of aggregates can occur.

The addition of chemical additives, such as denaturants, protein stabilizers, and protein aggregation inhibitors, has been described to prevent protein aggregation. Urea and GdnHCl are typical protein denaturants. At high concentrations, denaturants will denature proteins by the chaotropic effect and/or by interacting with the unfolded state, while at low denaturant concentrations, some denaturants have been reported to stabilize the structure of the target protein by inhibiting/destabilizing aggregates (Yamaguchi and Miyazaki 2014). $(NH_4)_2SO_4$ is a protein stabilizer that can stabilize protein structure at low concentration through electrostatic interactions, which changes the solubility of the native (folded) structure protein. However, protein destabilizers often accelerate protein aggregation. Arginine and its derivatives are among some of the amino acids classified as protein aggregation inhibitors. These amino acids are often used in the folding process, and are reported to increase yields by decreasing aggregation (Yamaguchi and Miyazaki 2014).

Some investigators have proposed microfluidics approaches as rapid and simple protein folding methods. In a microfluidic system, the laminar flow in microchannels is used to create a well-defined and predictable interfacial region. However, difficult-to-fold proteins can aggregate in the microchannels due to rapid removal of denaturant from the denatured proteins. Thus, microfluidic chips with rapid mixing are not always useful in the folding of difficult-to-fold proteins (Yamaguchi and Miyazaki 2014).

A need continues to exist in the art of pharmaceutical drug production and other technical areas related to protein/peptide recovery for more efficient methods for providing properly folded proteins. In particular, improved methods to obtain properly folded proteins from proteins within inclusion bodies (or other sources of protein that exist in an aggregated form), and methods that may be implemented in protein recycling techniques, remain needed. In addition, a reproducible and reliable method for producing a sufficient amount of important, yet difficult to fold complex protein assemblages, such as major histocompatability complex (MHC) proteins, their complexes with peptides and multimeric peptide/MHC complexes, is needed for facilitating drug/pharmaceutical development, immune disease treatment modalities, and biotechnological reagents.

SUMMARY

In a general and overall sense, the present invention provides a microscale method for efficiently and quickly producing a preparation of correctly folded recombinant proteins. In some embodiments, the proteins may be further described as particularly complex and difficult to fold, such as the class I MHC proteins and their complexes.

When expressed in bacteria (such as *E. coli*), the proteins that makeup class I MHC proteins, like many other recombinant proteins, assemble into bacterial inclusion bodies. These proteins within an inclusion body are in a biologically inactive form, and exist in an agglomerated state wherein the protein is "misfolded" (i.e., does not possess the folded protein configuration necessary to provide a biologically active protein). Standard procedures for obtaining properly folded proteins such as class I MHC proteins are time consuming, requiring several days, and cumbersome, as large volumes of multiple reagents are required. The present invention demonstrates a much less time consuming microscale method for producing properly folded complex proteins, such as MHC proteins and their complexes, that may be accomplished in less than 24 hours, using only a fraction of the buffers and other materials required in conventional methods.

In some embodiments, the method disclosed provides for the recombinant production of class I MHC heavy chain and $\beta_2$m separately within bacterial inclusion bodies. Solubilized preparations of these proteins are then processed according to the present invention by a series of steps that includes the in vitro folding of the proteins in the presence of a peptide that binds an MHC heavy chain at its antigen-binding site or other site.

In other embodiments, the method provides for the microscale production of soluble, stable and functional peptide/MHC complex in a process where folding can take 24 hours or less. In particular embodiments, the microscale method provides for the production of a properly folded preparation of a protein of interest by:

1. Diluting a small volume of the solubilized protein of interest with a small volume of a reaction buffer, such that the total volume of reaction buffer and solubilized protein does not exceed about 500 µl.
2. A microdialysis step that proceeds to completion in only about 2 hours.
3. A folded protein recovery process (such as for folded peptide/MHC) that is achieved by affinity between a protein tag (such as a His tag or other tag) and the protein of interest being recovered (e.g., His-tagged $\beta_2$m), and includes the use of a purification reagent (e.g., such as $Ni^{2+}$NTA magnetic beads, or magnetic beads coated with an antibody) or other affinity reagent. The present microscale method thereby eliminates the need for chromatographic protein purification techniques, and therefore avoids the complexity and protein loss attendant thereto.

In some embodiments, the folded protein may be eluted from a capture moiety, such as from magnetic beads, using a small volume of elution buffer, such as about 100 µl of a concentrated imidazole solution. In addition, the microscale folding method is accomplished in significantly shorter time periods, compared to existing folding methodologies (e.g., a single day or less compared to multiple days). The microscale protein folding method provided thus significantly reduces and/or eliminates at least three of the major disadvantages faced by the traditional protein production: operative time, volume, and cost.

In other embodiments, the microscale method provides for the incorporation of a detectable molecular tag, such as a histidine tag (6×-Histidine) on $\beta_2$-m or other complex protein of interest. The presence of the molecular tag provides for a simplification of the downstream purification of folded protein (such as folded peptide/MHC complex), and saves overall time and expense. Any number of different molecular tags may be employed in the present methods, including His (5 to 10 histidines), Myc, TC, V5, VSV, Halo, Nus, Fc, and any number of other molecular tags known to those of skill in the protein purification arts.

By way of example, and in some embodiments, the microscale method provides for folding a class I peptide/MHC complex in a small volume of about 500 µl for dialysis, and the recovery of the properly folded complex protein after a dialysis step of only about 2 hours at temperatures above 4° C. and less than 32° C., such as room temperature (25° C.).

In some embodiments, the microscale method comprises providing a source of aggregated protein of interest or a source of precipitated protein aggregate, or a source of misfolded or inactive solution. In one example, a source of aggregated protein of interest comprises inclusion bodies. Inclusion bodies from bacterial sources may comprise aggregated major histocompatibility complex heavy chain protein (MHC-HC) and $\beta_2$m protein, which may further include a peptide that binds at the antigen-binding or other site of the MHC. These inclusion bodies would first be solubilized by exposing the inclusion bodies to a denaturing agent, a reducing agent and a cysteine blocking agent. A small volume of these suspensions are then transferred in a particular order (typically $\beta_2$-m first followed by MHC-HC) into less than one milliliter of a folding buffer, the folding buffer comprising additives, a redox pair, proteolysis inhibitors and peptide or other MHC-HC binding molecule. This results in the generation of a protein suspension comprising diluted and partially folded/assembled MHC-HC and $\beta_2$-m.

The method then proceeds to a step wherein the small volume of diluted preparation is subjected to continuous stirring, followed by dialysis for less than 12 hours to obtain a protein suspension comprising folded and assembled peptide/MHC complex.

In another embodiment, inclusion bodies of $\beta_2$m alone are utilized and the MHC-HC and peptide that binds at the antigen-binding or other site of the MHC is excluded in order to produce folded $\beta_2$m protein.

In some embodiments, the ratio of protein to refolding buffer is 1:10 by volume, wherein a maximum volume of 500 microliters is not to be exceeded. In some embodiments of the method, the protein suspension is to be stirred constantly. For example, a magnetic stirrer capable of fitting in a nine-millimeter flat-bottomed tube may be used to provide continuous stirring.

In another aspect of the invention, the dialysis step comprises dialysis for about two hours at about 25° C. (room temperature). In some embodiments, the maximum volume of the dialysate is 500 milliliters. In another aspect of the invention, the dialysate is changed every half hour and contains a buffering agent. The dialysate may further be described as having a pH of between 7 and about 8.3. For ease of production, the dialysis may be performed using a commercially available mini-dialysis or micro-dialysis unit.

In one embodiment, the protein is an assembled peptide/MHC complex, i.e., a complex of MHC-HC, $\beta_2$m, and a peptide or other molecule bound in the MHC-HC binding groove. In some embodiments, the $\beta_2$m is modified with a C-terminal hexahistidine tag that allows the folded protein to be separated from the suspension by adding $Ni^{2+}$-NTA magnetic beads to the suspension. In one embodiment, the $Ni^{2+}$-NTA magnetic beads are washed with 1 mL of the dialysate and the folded protein is eluted from the $Ni^{2+}$-NTA magnetic beads with about 100 microliters eluent solution. By way of example, the eluent solution may comprise a buffering agent, salt, metalloprotease inhibitor and azole heterocycle with a pH of 8.0. Further, and by way of example, the azole heterocycle is imidazole at a concentration of 0.3 molar or less, and is removed by dialysis that is continued for two hours. In another aspect of the invention, the dialysis is performed against the eluent with surfactant having a pH of 8.3 without the imidazole.

These and other features of the present teachings are set forth herein.

BRIEF DESCRIPTION OF THE FIGURES

FIG. 1A-1D. The Tm (melting temperature) of a peptide/MHC complex generated by the microscale folding procedure is essentially the same as the Tm of the same peptide/MHC complex generated by the standard procedure. FIG. 1A) DSF analysis as fluorescence intensity vs. temperature for protein from the microscale folding procedure performed as described in Examples 1 and 2. FIG. 1B) First derivative of the data in FIG. 1A, along with a fit to the data (red line). The Tm is indicated along with its standard fitting error. FIG. 1C). DSF analysis as fluorescence intensity vs. temperature for protein from a standard folding procedure performed as described in Examples 1 and 2. FIG. 1D). First derivative of the data in panel FIG. 1C, along with a fit to the data (red line). The Tm is indicated along with its standard fitting error. The small difference in Tm between the result in panels FIG. 1B and FIG. 1D is attributable to the lower protein concentration and, therefore, reduced signal in the date in panel FIG. 1A compared to the data in panel FIG. 1b and is not significant.

FIG. 3A) DSF analysis as fluorescence intensity vs. temperature as described in Example 1 and 3. FIG. 3B) First derivative of the data in FIG. 3A, along with fit to the data (red line). The Tm is indicated along with its standard fitting error.

DETAILED DESCRIPTION

Figure 2:
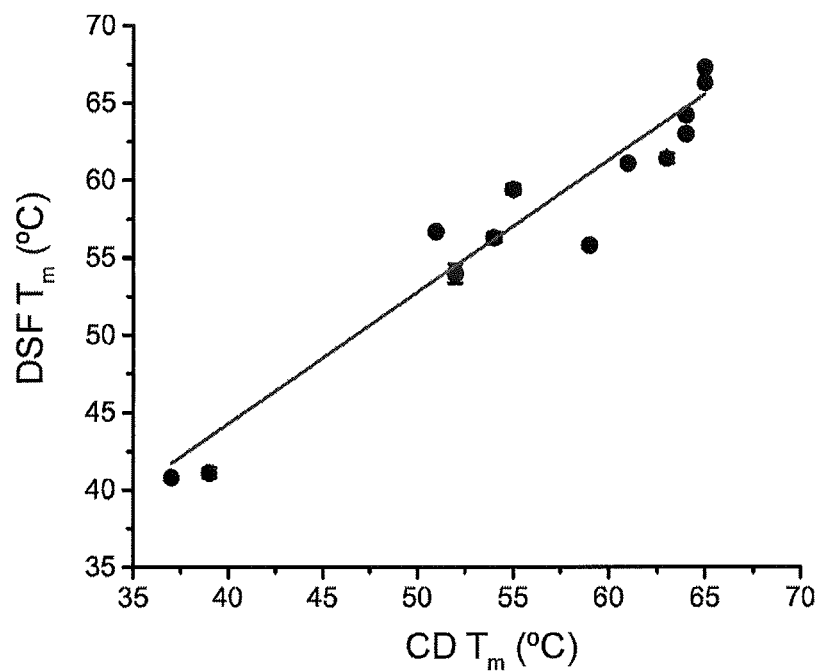
FIG. 2 Tm values of different peptide/MHC complexes determined by DSF and by CD are equivalent within accepted error limits.

Although the instant disclosure is described in detail below, it is to be understood that disclosure is not limited to the particular methodologies, protocols and reagents described herein as these may vary. It is also to be understood that the terminology used herein is for the purpose of describing particular embodiments only, and is not intended to limit the scope of the instant disclosure, which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they might be combined in any manner and in any number to create additional embodiments. The variously described examples and preferred embodiments should not be construed to limit the present disclosure to only the explicitly described embodiments. This description should be understood to support and encompass embodiments, which combine the explicitly described embodiments with any number of the disclosed and/or preferred elements. Furthermore, any permutations and combinations of all described elements in this application should be considered disclosed by the description of the present application unless the context indicates otherwise.

The practice of the instant disclosure will employ, unless otherwise indicated, conventional methods of chemistry, biochemistry, and recombinant DNA techniques which are explained in the literature in the field (e.g., Molecular Cloning: A Laboratory Manual, 2nd Edition, J. Sambrook et al. eds., Cold Spring Harbor Laboratory Press, Cold Spring Harbor 1989).

Throughout this specification and the claims which follow, unless the context requires otherwise, the word "comprise" and variations, such as "comprises" and "comprising," will be understood to imply the inclusion of a stated member, integer, or step or group of members, integers, or steps, but not the exclusion of any other member, integer, or step or group of members, integers, or steps. The term "comprise" also encompasses the terms "essentially consisting of" and "consisting of" unless the context clearly dictates otherwise. As used in this specification and the appended claims, the singular forms "a," "an," and "the" include plural referents, unless the context clearly dictates otherwise.

Definitions

"Host cell" includes unicellular cells such as bacteria and yeast, or other suitable cells such as animal and plant cells, which have been transformed to express a foreign polypeptide.

"Foreign polypeptides" are polypeptides coded for by a non-native or heterologous segment of DNA not normally found in the wild-type host cell.

"Inclusion bodies" refers to the insoluble cytoplasmic aggregates containing foreign polypeptides often found in transformed cells.

The "conformation" of a polypeptide describes the three dimensional structure of the polypeptide's amino acid chains.

"Conformation factors" are forces influencing a polypeptide's conformation, and include steric interactions, charge interactions, hydrophobic interactions and disulfide bond linkages.

"Biological activity" means that a polypeptide is in a conformation such that it is capable of effecting its intended in vivo physiological response, and exhibits activity in biological assays.

As used in the description of the present invention, the term "microscale" relates to performing a protein folding reaction in a volume of less than 1 milliliter (ml).

As used in the description of the present invention, the phrase "a protein of interest" relates to a complex protein, a simple protein, or a protein complex comprising an assembly between one protein chain, one or more additional protein chains, and/or other molecule or molecules, such as a peptide, lipid, glycolipid or metabolite.

"Solubilizing agents" are chaotropes such as guanidine hydrochloride or urea and also include reductants such as DTT, or mixtures thereof. These solubilizing agents to at least some extent denature or unfold polypeptides, thus rendering them soluble.

A "solubilized polypeptide solution" refers to a solution formed by mixing a polypeptide with a solubilizing agent such that the resulting polypeptide solution comprises the polypeptide in some stage of unfolding, depending on the particular solubilizing agent employed.

"Solubilized polypeptide" refers to a polypeptide unfolded to some degree.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The instant disclosure provides a method of in vitro folding of solubilized proteins, permitting efficient folding of the proteins to provide a biologically active protein conformation, where the folded protein produced by the process exhibits the characteristic biological activity of the corresponding native protein.

EXAMPLES

In order that the disclosure described herein may be more fully understood, the following examples are set forth. It should be understood that these examples are for illustrative purposes only and are not to be construed as limiting this invention in any manner.

Example 1

Materials and Methods: Protein Folding, Fluorimetry, and Spectroscopy

In this example, protein complexes including recombinant MHC-HC HLA-A2, $\beta_2$m protein, and an MHC-binding peptide were used. In their native state, these three proteins form a complex protein.

Recombinant MHC-HC HLA-A2 and b$_2$m protein were expressed as inclusion bodies in *Escherichia coli*. These inclusion bodies were solubilized by exposure to a denaturing agent and a reducing agent. The sequence of b$_2$m included a C-terminal hexahistidine tag. Peptides that may be used in this process include any peptide that binds to class I MHC. These peptides may be synthesized chemically, purified to greater than 95%, and verified by mass spectrometry. An exemplary list of these peptides include the Tax peptide (epitope ID 37257 in the Immune Epitope Database), the MART-1 decamer peptide (epitope ID 10987 in the Immune Epitope Database), or any previously identified or novel antigenic peptide or peptide variant associated with or suspected to be associated with normal or abnormal immune responses.

Standard scale folding from inclusion bodies was performed according to standard procedures in the literature for production of peptide/MHC complexes (Davis-Harrison, Armstrog et al. 2005). Using the solubilized inclusion bodies, to 1 L of folding buffer supplemented with peptide at a concentration of 30 micromolar, MHC-HC HLA-A2 was added to yield a concentration of 1 micromolar and $\beta_2$m was added to yield a concentration of 2.5 micromolar. The reaction was incubated and stirred for 24 hours at 4° C., then dialyzed against 10 liters of 10 millimolar Tris-HCl (pH 8.3) for 24 hours at room temperature. Folded and assembled peptide/MHC complex was purified using ion exchange followed by size-exclusion chromatography.

Microscale folding was performed in a volume of 100 microliters of folding buffer supplemented with 150 micromolar peptide. $\beta_2$m from the solubilized inclusion bodies was added to yield a concentration of 12.5 micromolar. The reaction was incubated for 1 hour at 4° C. with constant stirring. Then MHC-HC HLA-A2 from the solubilized inclusion bodies was added to yield a concentration of 5 micromolar, and the mixture incubated with stirring for 12 hours at 4° C. The reaction was then subjected to microdialysis against a 7000 molecular weight cutoff membrane for 2 hours at room temperature with constant stirring in dialysis buffer. Dialysis buffer was exchanged every 30 minutes. Folded and assembled peptide/MHC complex was subsequently captured by addition of Ni$^{2+}$-NTA magnetic beads. The beads were washed with dialysis buffer twice and protein was eluted with 10 millimolar HEPES (pH 8.0), 150 millimolar NaCl, 3 millimolar EDTA, 300 millimolar imidazole. A second round of dialysis was used to remove the imidazole. Protein concentration determined was spectrophotometrically, and the protein was analyzed without further purification.

Differential scanning fluorimetry was performed using an Applied Biosystems StepOnePlus real-time polymerase chain reaction instrument with the excitation and emission wavelengths set to 587 and 607 nanometers, respectively. Solution volumes were 20 microliters in 96-well plates. Assay buffer was 10 micro molar HEPES (pH 7.4), 150 micro molar NaCl, 3 micro molar EDTA, with 0.005% surfactant P20 added to prevent protein adherence to the plate. Protein and SYPRO orange (Invitrogen) concentrations were varied as needed. The temperature range spanned 25° C. to 95° C. Data analysis was performed in OriginPro 9. Tm (melting temperature) values were determined by identifying the point at which the transition was 50% complete using the temperature derivative of the melting curve.

For protein produced by the standard scale folding method, the derivative curve was processed with the interactive single peak processing algorithm in OriginPro, applying a sigmoidal baseline and fitting the peak to determine the Tm and its error. A bi-Gaussian function, commonly used in spectroscopy and chromatography, was used for peak fitting as the peaks were noticeably skewed, presumably due to the irreversible nature of class I peptide/MHC thermal denaturation. The fitting procedure was modified for protein produced at the microscale, as the reduced signal to noise ratio in the derivative curve led to minor transitions outside of the major transition that confounded the single-peak processing algorithm. The data were subject to the automated multiple peak fitting process in OriginPro, using default options except that bi-Gaussian functions were used. The multiple peak fitting process was successful in identifying the major transitions and their associated Tm and standard error.

CD spectroscopy was performed using a Jasco J815 instrument. Temperature was increased from 10° C. to 100° C. at an increment of 1° C./min, monitoring a wavelength of 218 nanometers. Protein concentrations were between 5 micro molar and 10 micro molar in 20 millimolar phosphate (pH 7.4), 75 millimolar NaCl. Data analysis was performed in Kaleidagraph 3.08 or OriginPro 9. Data in the transition region were fit to a six-order polynomial, and the point at which the transition was 50% complete determined Tm values.

Example 2

Comparison of Differential Scanning Fluorimetry (DSF) and Circular Dichroism (CD)

Quantifying the strength of the interactions between peptides and major histocompatibility complex (MHC) proteins is important in the identification of T cell epitopes and evaluating the consequences of naturally occurring or engineered peptide modifications (Trolle, Metushi et al. 2015). For most class I MHC proteins, the significant instability of the peptide-free "empty" protein has hindered direct measurements of peptide-MHC binding equilibrium constants.

Measurements of peptide-MHC thermal stability is used as a proxy for peptide binding affinity. Measurements of peptide-MHC thermal stability have been used as a standard, with circular dichroism (CD) spectroscopy being the most frequent mode of detection (Morgan, Holton et al. 1997). CD is used to monitor the loss of alpha-helical character in the peptide binding domain as the complex dissociates and unfolds.

A drawback of CD-monitored thermal unfolding of peptide-MHC complexes is the limited signal-to-noise ratio and the large amount of sample required, typically at least hundreds of microliters of protein at concentrations of at least tens of micromolar). Although these sample requirements may be small relative to the significant amount of protein typically generated for structural studies, these requirements reduce throughput and limit the use of thermal stability measurements in broader studies, such as epitope discovery.

As opposed to CD spectroscopy, an alternative method to assess protein stability is differential scanning fluorimetry (DSF). DSF takes advantage of small environmentally-sensitive fluorescent molecules whose fluorescence is enhanced when specifically bound to exposed hydrophobic surfaces such as those created by protein unfolding (Simenov 2013). Primary advantages of DSF are the small volumes and reduced amounts of protein required compared to CD spectroscopy. The microscale protein folding technique described herein is very well suited to producing peptide/MHC samples rapidly and on a small scale for analysis by DSF.

The present example demonstrates the determination by DSF of the Tm of a peptide/MHC sample produced by the microscale protein folding method and the standard folding method. Following the methods in Example 1, a peptide/MHC complex, consisting of the Tax peptide (epitope ID 37257 in the Immune Epitope Database) the MHC-HC HLA-A2, and $b_2m$, was produced by microscale folding and standard folding and subjected to DSF analysis (See FIG. 1A-FIG. 1D). The resulting Tm values determined by both approaches are the same within error.

To demonstrate that peptide/MHC values determined by DSF correlate with those determined by CD, Tm values were determined for several peptide/MHC complexes by both techniques. As shown in FIG. 2, the two values are tightly correlated, indicating that DSF is a suitable alternative to CD spectroscopy that requires substantially less sample.

Example 3

Analysis of $\beta_2m$ Protein Produced by Microscale Protein Folding

Figure 3A:
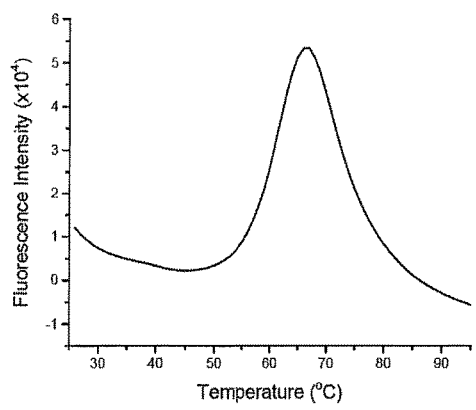
FIG. 3A-FIG. 3B. Analysis of $\beta_2$_m alone produced by the microscale folding procedure.
Figure 3B:
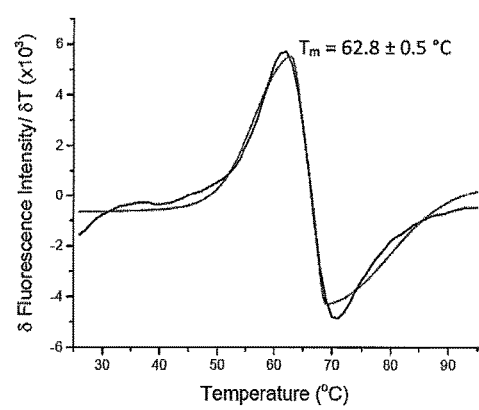
Figure 4:
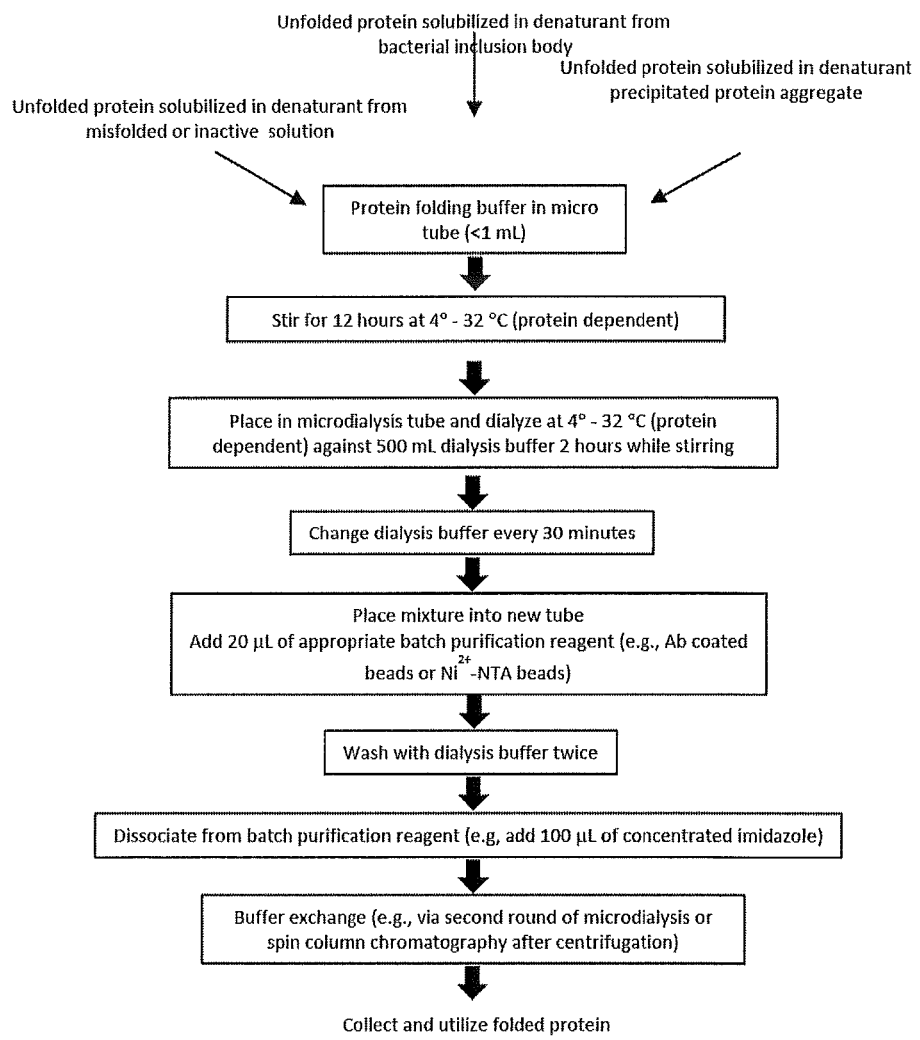
FIG. 4. Flow chart for microscale protein folding.

To verify that the microscale protein folding method is useful for producing proteins other than class I peptide/MHC complexes, the microscale folding reaction described in Example 1 was modified to produce only the protein $\beta_2m$. Purified $\beta_2m$ was denatured in 6 M guanidine-HCl solution to a final concentration of 500 micromolar and heated to 37° C. for 30 minutes. Microscale folding was performed in a volume of 100 microliters with constant stirring, adding denatured $\beta_2m$ to yield a protein concentration of 12.5 micromolar. The reaction was then stirred for 12 hours at 4° C. Microdialysis was then performed against a high molecular weight cutoff membrane, such as a 7 kilodalton molecular weight cutoff membrane at room temperature for 2 hours with the buffer exchanged every 30 minutes. A second round of dialysis was used to exchange the folded $\beta_2m$ into the final buffer for 2 hours at 4° C. with constant stirring and buffer exchange every 30 minutes, concentration determined spectrophotometrically, and the protein was analyzed determined by differential scanning fluorimetry without further purification. DSF analysis of $\beta_2m$ produced by the microscale folding reaction technique is shown in FIG. 3.

Example 4

Automation of Microscale Folding for Production and Analysis of Peptide/MHC Complexes There exists significant interest in the analysis of peptide/MHC complexes, for example for immune epitope discovery and validation. Measurements of peptide-MHC interactions are often used to facilitate these areas of investigation. Frequently, this requires that tens, hundreds or more peptides be examined for their individual interactions with one or more MHC proteins. The microscale folding procedure described herein readily lends itself to an automated process which would facilitate such work, particularly, although not necessarily, when coupled with a high throughput analysis procedure such as DSF.

An example of one practical application of the automated microscale folding technique is provided here with peptide/MHC production.

Figure 5:
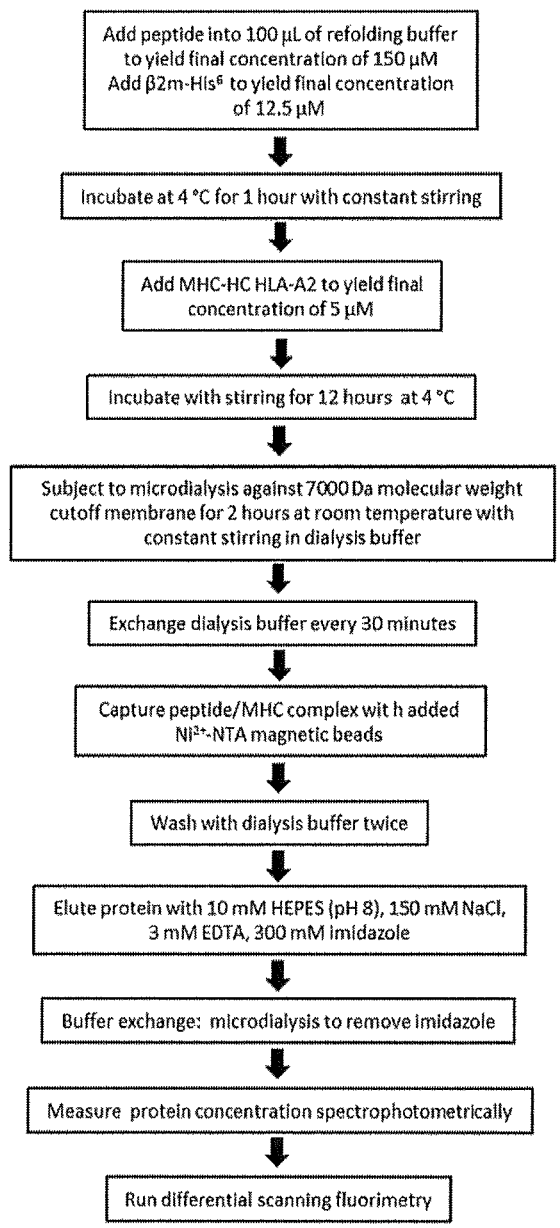
FIG. 5. Flowchart for microscale folding and assembly of class I peptide/MHC complexes, where the MHC-HC is HLA-A2.

Following the example of the microscale folding procedure outlined in Example 1 and outlined in FIG. 5, a commercially available liquid handling robot in a temperature controlled environment would dispense denaturant solubilized $\beta_2$m into each well of a sealable multi-well plate, such as a 16, 96, 384, or more multi-well plate. Wells in the plate would be pre-loaded with protein folding solution and the desired peptides for analysis, or these could be added by the same, or another, liquid handling robot prior to addition of $\beta_2$m modified by a C-terminal hexahistidine tag. The plate would be robotically sealed. The plate would then be agitated for the appropriate time by the same, or another, plate handling robot in a temperature controlled environment to mix the contents of the wells in the plate. This would facilitate the mixing achieved by the stirring, as described in Example 1. Commercially available plate mixers may also be used. It is anticipated that the agitation time and temperature may vary slightly from Example 1 given the differences in mixing efficiencies expected between single tubes and multi-well plates.

After appropriate agitation, the plate cover would be robotically removed and denaturant-solubilized MHC-HC added by the same liquid handling robot used to dispense $\beta_2$m. The plate would again be sealed and agitated for the appropriate time as described in the preceding paragraph. It is anticipated the agitation time and temperature may vary slightly from Example 1 given the differences in mixing efficiencies expected between single tubes and multi-well plates.

After appropriate agitation, the contents of each well in the plate could be transferred to an appropriate, commercially available multi-well microdialysis plate using a liquid handling robot. Dialysis would then proceed as described in Example 1. Dialysis solution would be changed by the liquid handling robot. It is anticipated that dialysis time and temperature may vary slightly from Example 1 given the differences in dialysis efficiencies expected between single tubes and multi-well plates.

After dialysis is complete, the liquid handling robot would add $Ni^{2+}$-NTA beads to capture the folded and assembled peptide/MHC protein, and the plate agitated as described in the preceding paragraphs. After agitation, the plate will be robotically transferred to a centrifuge compatible with multiwell plates and centrifuged to pellet the protein-coated beads. After centrifugation, the plate could be robotically transferred back to the same, or another, liquid handling robot and imidazole solution added to elute protein. After incubation for an appropriate time, the plate could again be robotically transferred back to the centrifuge to collect the beads. After centrifugation is complete the plate could again be transferred back to the same, or another, liquid handling robot to remove the protein solution from each well.

For analysis of peptide binding to MHC by DSF, after it is robotically removed from the $Ni^{2+}$-NTA beads, the protein would be transferred to a multi well plate compatible with a RT-PCR instrument compatible with DSF, or a multiwell plate compatible with a commercially available DSF instrument. The plate could be transferred to the instrument and the Tm of each sample determined.

Table 1 provides a non-exhaustive listing of some of the major elements from 1) standard method of class I MHC folding and assembly and 2) microscale folding of class I MHC and assembly.

TABLE 1

| Standard scale folding of peptide/MHC from inclusion bodies | Microscale folding of peptide/MHC from inclusion bodies |
| --- | --- |
| Inclusion body consisting of heavy chain and $\beta_2$ microglobulin ($\beta$2m). | Inclusion body consisting of heavy chain and $\beta_2$ microglobulin ($\beta$2m). $\beta_2$m modified with a C-terminal 6X-His tag |
| Solubilization Buffer: <br> MES, pH 6.5 <br> EDTA <br> DTT <br> 8M Urea | Solubilization Buffer: <br> 50 mM MES, pH 6.0 <br> 0.1 mM EDTA <br> 0.1 mM DTT <br> 8M Urea |
| Pre-equilibration of peptide and $\beta_2$m for one hour prior to addition of HLA under constant stirring at 4° C. with folding buffer. | Pre-equilibration of peptide and $\beta_2$m for one hour prior to addition of HLA under constant stirring at 4° C. with folding buffer. |
| Ratio: 1:2:10 (heavy chain:$\beta_2$m:peptide) | Ratio: 1:2.5:30 (heavy chain:$\beta_2$m:peptide) |
| Dilution with folding buffer: <br> 100 mM Tris (pH 8-8.3) <br> 400 mM L-arginine <br> 2 mM EDTA <br> 6.3 mM cysteamine <br> 3.7 mM cystamine <br> 0.2 mM PMSF | Dilution with folding buffer: <br> 100 mM Tris-HCl (pH 8-8.3) <br> 400 mM L-arginine-HCl <br> 2 mM EDTA <br> 6.3 mM cysteamine <br> 3.7 mM cystamine <br> 0.2 mM PMSF |
| Incubation for 24 h at 4° C. with stirring | Incubation overnight at 4° C. with stirring |
| N.A | Dilution volume 500 ul |
| Labware capable of holding up to a few liters solution | 9 mm flat bottomed tubes (capacity 1.8 ml) |
| Dialysis for 1-2 days at room temperature | Dialysis for 2 hr at room temperature |
| Dialysis using 6000-8000 Da MW cutoff dialysis membrane | Dialysis using 7000 Da MW cutoff dialysis membrane |
| Dialysate volume: Liters | Dialysate volume: 500 ml |
| Dialysis Buffer: <br> 10 mM Tris-HCl (pH 8.3) | Dialysis Buffer: <br> 10 mM Tris-HCl (pH 8.3) |

TABLE 1-continued

| Standard scale folding of peptide/MHC from inclusion bodies | Microscale folding of peptide/MHC from inclusion bodies |
|---|---|
| Dialysis buffer changed multiple times<br>Folded protein subjected to anion exchange followed by size-exclusion chromatography | Dialysis buffer changed every 30 min<br>Folded protein captured by addition of 20 μL of Ni2+-NTA magnetic beads.<br>Beads washed with 1 mL of dialysis buffer<br>Folded protein eluted from beads using 100 ul elution buffer:<br>10 mM HEPES (pH 8.0)<br>150 mM NaCl<br>3 mM EDTA<br>300 mM imidazole<br>Folded protein subjected to dialysis using dialysis buffer:<br>10 mM HEPES (pH 8.0)<br>150 mM NaCl<br>3 mM EDTA<br>0.005% Surfactant P20 |

BIBLIOGRAPHY

1. U.S. Pat. No. 4,620,948
2. U.S. Pat. No. 4,530,787
3. EP Pat 0512097
4. EP 0364926
5. EP 0219874
6. WO 01/87925
7. WO/1986/005809
8. U.S. Pat. No. 6,007,820
9. Reid, S W, et al. (1996), FEBS Lett. March 25: 383 (1-2): 119-123.
10. US2004011663
11. U.S. Pat. No. 8,703,123
12. Burgess, R. R. (2009). Chapter 17 Refolding Solubilized Inclusion Body Proteins. *Methods in Enzymology*. R. B. Richard and P. D. Murray, Academic Press. Volume 463: 259-282.
13. Davis-Harrison, R. L., K. M. Armstrong and B. M. Baker (2005). "Two Different T Cell Receptors use Different Thermodynamic Strategies to Recognize the Same Peptide/MHC Ligand." *Journal of Molecular Biology* 346(2): 533-550.
14. Morgan, C. S., J. M. Holton, B. D. Olafson, P. J. Bjorkman and S. L. Mayo (1997). "Circular dichroism determination of class I MHC-peptide equilibrium dissociation constants." *Protein Science* 6(8): 1771-1773.
15. Seras-Franzoso, J., S. Peternel, O. Cano-Garrido, A. Villaverde and E. García-Fruitód (2015). Bacterial Inclusion Body Purification. *Insoluble Proteins*. E. García-Fruitós, Springer New York. 1258: 293-305.
16. Simeonov, A. (2013). "Recent developments in the use of differential scanning fluorometry in protein and small molecule discovery and characterization." *Expert Opinion on Drug Discovery* 8(9): 1071-1082.
17. Singh, S. M. and A. K. Panda (2005). "Solubilization and refolding of bacterial inclusion body proteins." *Journal of Bioscience and Bioengineering* 99(4): 303-310.
18. Trolle, T., I. G. Metushi, J. A. Greenbaum, Y. Kim, J. Sidney, O. Lund, A. Sette, B. Peters and M. Nielsen (2015). "Automated benchmarking of peptide-MHC class I binding predictions." *Bioinformatics* 31(13): 2174-2181.
19. Yamaguchi, H. and M. Miyazaki (2014). "Refolding Techniques for Recovering Biologically Active Recombinant Proteins from Inclusion Bodies." *Biomolecules* 4(1): 235.

What is claimed is:

1. A method for microscale production of a complex protein comprising at least a first protein of interest and a second protein of interest, wherein at least one protein of interest is a recombinant protein, comprising the steps of:
   diluting a denatured solubilized protein preparation comprising a first protein of interest to provide a diluted preparation;
   dialyzing the diluted preparation at a temperature of between 4° C. and 32° C. for 1 to 3 hours to provide a first correctly folded first protein of interest preparation; and
   adding a volume of a second protein of interest to the first protein of interest preparation to form a complex protein preparation comprising the complex protein;
   adding the complex protein preparation to a purification reagent, the purification reagent capable of capturing the complex protein; and
   obtaining the complex protein,
   wherein the complex protein has a biologically active folded protein structure, said method is completed in less than 24 hours,
   at least one protein of interest comprises $\beta_2$-microglobulin ($\beta_2$m), a class I major histocompatibility complex protein heavy chain (MHC-HC), or a class I MHC binding molecule, and
   wherein each preparation has a final volume of less than 1 milliliter.

2. The method of claim 1, wherein the complex protein preparation is purified by a chromatographic method or by a buffer exchange method.

3. The method of claim 1, wherein said first protein of interest is a recombinant protein and the diluted preparation has a volume of not more than 500 microliters.

4. The method of claim 3, wherein the recombinant protein is $\beta_2$m or MHC-HC.

5. The method of claim 3, wherein said first preparation of said protein of interest is incubated with an MHC-binding molecule.

6. The method of claim 1 wherein at least one protein of interest is a class I MHC binding molecule, and said class I MHC binding molecule is a peptide, lipid, glycolipid, metabolite or other molecule having binding affinity for a class I MHC protein.

7. The method of claim 1 wherein the purification reagent is Ab coated beads.

8. The method of claim 1, wherein said denatured solubilized protein of interest is diluted in a folding buffer in a ratio of between 1:5 to 1:50 by volume.

9. The method of claim 1, wherein the complex protein preparation is purified by size-exclusion column chromatography, hydrophobic interaction chromatography, ion exchange chromatography, column chromatography, affinity chromatography, or batch purification.

10. The method of claim 1 wherein the first protein of interest is provided from denatured solubilized bacterial inclusion bodies, a precipitated protein aggregate, or a misfolded or inactive protein solution.

11. The method of claim 1 wherein said complex protein comprises a detectable tag having affinity for the purification reagent.

12. A microscale production method for preparing peptide/MHC complexes comprising:
    combining a MHC binding molecule of interest with a small volume of folding buffer, and adding a molecular tagged preparation of $\beta_2$m sufficient to yield a final concentration of about 12.5 μM, so as to provide a solubilized first preparation;
    incubating said first preparation for 1 hour;
    adding MHC-HC to said first preparation so as to provide a final concentration of 5 μM, to provide a second preparation;
    incubating said second preparation for 12 hours;
    dialyzing said second preparation for 2 hours at 4° C. to about 32° C., to provide a third preparation;
    adding said third preparation to a volume of a purification reagent having affinity for the detectable molecular tag to provide a fourth preparation comprising a captured tagged peptide/MHC complex;
    eluting the captured tagged peptide/MHC complex with an elution buffer to provide a fifth preparation comprising partially purified protein complex; and
    removing contaminating reagents from the fifth preparation to provide a peptide/MHC complex suitable for analysis;
    wherein each preparation has a volume of less than 1 milliliter.

13. The microscale production method of claim 12 wherein said purification reagent comprises Ab coated beads.

14. The microscale production method of claim 12 wherein said fourth solution is incubated for 12 hours at a temperature of 4° C.

15. The microscale production method of claim 12 wherein said eluting buffer comprises mixture of 10 mM HEPES (pH 8), 150 mM NaCl, 3 mM EDTA, and 300 mM imidazole.

16. The microscale production method of claim 12 wherein said second preparation is dialyzed against a dialysis membrane having a 7 kDa molecular weight cutoff membrane.

17. The microscale production method of claim 12, wherein the detectable molecular tag is Histidine.

* * * * *